United States Patent
Han et al.

(10) Patent No.: US 11,369,698 B2
(45) Date of Patent: Jun. 28, 2022

(54) TUMOR-TARGETING, CLEARABLE HUMAN PROTEIN-BASED MRI NANOPROBES, AND COMPOSITIONS AND METHODS THEREOF

(71) Applicant: University of Massachusetts, Boston, MA (US)

(72) Inventors: Gang Han, Shrewsbury, MA (US); Yang Zhao, Worcester, MA (US)

(73) Assignee: University of Massachusetts, Boston, MA (US)

( * ) Notice: Subject to any disclaimer, the term of this patent is extended or adjusted under 35 U.S.C. 154(b) by 32 days.

(21) Appl. No.: 16/608,837

(22) PCT Filed: May 17, 2018

(86) PCT No.: PCT/US2018/033071
§ 371 (c)(1),
(2) Date: Oct. 27, 2019

(87) PCT Pub. No.: WO2018/213518
PCT Pub. Date: Nov. 22, 2018

(65) Prior Publication Data
US 2020/0197543 A1 Jun. 25, 2020

Related U.S. Application Data

(60) Provisional application No. 62/508,417, filed on May 19, 2017.

(51) Int. Cl.
*A61K 49/14* (2006.01)
*A61K 49/18* (2006.01)

(52) U.S. Cl.
CPC .......... *A61K 49/1866* (2013.01); *A61K 49/14* (2013.01)

(58) Field of Classification Search
CPC . A61K 49/14; A61K 49/1866; A61K 49/1869
See application file for complete search history.

(56) References Cited

U.S. PATENT DOCUMENTS

| | | | | |
|---|---|---|---|---|
| 2005/0153875 | A1* | 7/2005 | Bauer | A61K 47/644 424/130.1 |
| 2010/0015051 | A1* | 1/2010 | Labhasetwar | A61P 35/00 424/1.69 |

OTHER PUBLICATIONS

Huedayi Korkuzus et al., Transferrin-Coated Gadolinium Nanoparticles as MRI Contrast Agent, Mol. Imaging Biol, 15, 148-154. (Year: 2013).*
Hang J Choi et al. Mechanism of active targeting in solid tumors with transferrin-containing gold nanoparticles, PNAS, 1235-1240. (Year: 2010).*
Jean-Luc Bridot et al., Hybrid Gadolinium Oxide Nanoparticles: Multimodal Contrast Agents for in Vivo Imaging, JACS, 129, 5076-5084. (Year: 2007).*
Korkusuz et al. Transferrin-coated gadolinium nanoparticles as MRI contrast agent, Mol. Imaging and Biol, 15(2), 148-154. (Year: 2013).*
EP18802597.7 Extended European Search Report, dated Jan. 29, 2021.
Jiali Cai et al. "A transferrin-target magnetic/fluorescent dual-mode probe significantly enhances the diagnosis of non-small cell lung cancer" Oncotarget, vol. 7, No. 26, 40047-40059, Jun. 28, 2016.
Bingxin Gu et al. "99m Tc-labeled and gadolinium-chelated transferrin enhances the sensitivity and specificity of dual-modality SPECT/MR imaging of breast cancer" RSC Advances, vol. 6, No. 25, 20532-20541, Jan. 29, 2016.
Yang Zhao et al. "Tumor-Tragted and Clearable Juman Protein-Based MRI Nanoprobes" Nano Letters, vol. 17, No. 7, 4096-4100, Jun. 26, 2017.
Korkusuz et al. "Transferrin-Coated Gadolinium Nanoparticles as MRI Contrast Agent" Molecular Imaging and Biology, vol. 15, No. 2, 148-154, Jul. 19, 2012.

\* cited by examiner

*Primary Examiner* — Michael G. Hartley
*Assistant Examiner* — Jagadishwar R Samala
(74) *Attorney, Agent, or Firm* — Milstein Zhang & Wu LLC

(57) ABSTRACT

The invention provides a novel class of clearable, tumor-targeting and human protein-based MRI nanoprobes and contrast agents and their compositions, and methods of preparation and use thereof.

8 Claims, 13 Drawing Sheets

TUMOR-TARGETING, CLEARABLE HUMAN PROTEIN-BASED MRI NANOPROBES, AND COMPOSITIONS AND METHODS THEREOF

PRIORITY CLAIMS AND RELATED APPLICATIONS

This application is the U.S. national phase of and claims priority to PCT/US18/33071, filed May 17, 2018, which claims the benefit of priority from U.S. Provisional Application Ser. No. 62/508,417, filed on May 19, 2017, the entire content of each of which is incorporated herein by reference.

TECHNICAL FIELDS OF THE INVENTION

The invention generally relates to diagnostics and MRI contrast agents. More particularly, the invention relates to a novel class of clearable, tumor-targeting and human protein-based MRI nanoprobes and contrast agents and their compositions, and methods of preparation and use thereof.

BACKGROUND OF THE INVENTION

Magnetic resonance imaging (MRI), a medical imaging technique used in radiology, is one of the most used non-invasive and versatile imaging modalities for clinical detection, staging, and monitoring treatment of tumors. MRI affords unique advantages, for example, high spatial resolution, outstanding soft tissue contrast, and no radiation damage.

MRI, however, often encounters an inherent shortage of low sensitivity since there is little difference between normal and abnormal soft tissues in relaxation time and the resulting contrast. To overcome this drawback, materials that possess magnetic properties, namely MRI contrast agents (MRI-CAs), have been used to enhance imaging quality and signal contrast of MRI. As reported, more than 40% of all MRI examinations utilize a contrast agent. Development of magnetic contrast agents (CAs) has improved the inherent sensitivity of MRI, enabling this technique to visualize specific biological processes at both cellular and molecular levels. (Sun, et al. 2008 *Adv. Drug Delivery Rev.* 60, (11), 1252-65; Zhang, et al. 2016 *Nanoscale* 8, (20), 10491-510.)

Currently, the most frequently used magnetic CAs in clinical settings are Gd-based chelates due to their signal-enhancing positive contrast ability and negligible immunogenicity. Such Gd-based compounds, however, often suffer from short life spans, relatively low relaxivity, and the consequent need for high doses of intravenous administration, as well as the problematic gadolinium retention within vital organs. (Caravan, et al. 1999 *Chem Rev.* 99, (9), 2293-352; Na, et al. 2009 *J. Mater. Chem.* 19, (35), 6267; McDonald, et al. 2015 *J. Radiology* 275, (3), 772-82; Tu, et al. 2012 *Wiley Interdiscip. Rev.: Nanomed. Nanobiotechnol.* 4, (4), 448-57.)

To overcome these drawbacks, inorganic based Gd-containing nanoparticles, for examples, gadolinium oxide, gadolinium fluoride, and gadolinium phosphate, have been explored in attempts to enhance MR imaging quality. While such nanoparticles enjoy large longitudinal relaxation, enhanced sensitivity, prolonged circulating time and facile chemical modifications, their long-term stability, biocompatibility and clearance remain largely unclear, hindering their further biomedical applications. (Zhang, et al. 2016 *Nanoscale* 8, (20), 10491-510; McDonald, et al. 2015 *J. Radiology* 275, (3), 772-82; Longmire, et al. 2008 *Nanomedicine (Lond)*. 3, (5), 703-717; Chen, et al. 2014 *Small* 10, (18):3603-11.)

Therefore, the development of nontoxic, biocompatible and effective MRI-CAs plays an important role in expanding and improving MRI clinical applications. It remains challenging and highly desirable to develop a biocompatible tumor-targeting, as well as systemically clearable and more efficient Gd-based nanoparticle MRI CAs.

SUMMARY OF THE INVENTION

The invention provides a novel class of MRI CAs that, not only possess superior paramagnetic properties compared to conventional Gd-based contrast agents, but also exhibit excellent biocompatibility, negligible immunogenicity, and outstanding tumor-targeting and body-clearable abilities.

The invention offers a new approach to biocompatible multifunctional MRI contrast agents useful for a wide range of clinical imaging and treatment applications. Biocompatibility, targeting, and clearance are key challenges in the design of new MRI contrast agents. The invention provides a tumor-targeting, gadolinium biomineralized human transferrin (Tf) protein-based nanoparticle (Gd@Tf NP) for MRI use.

As compared to the conventionally used gadolinium chelates, the Gd@Tf NPs disclosed herein possess outstanding chemical stability and exhibited superior longitudinal relaxation. As demonstrated herein, Gd@Tf retains the natural tumor targeting ability and the subsequent tumor retrieval biofunctions of Tf. Thus, the Tf protein-based MR NPs integrate T1 signal amplification, precise tumor targeting, and systematic clearance capabilities.

In one aspect, the invention generally relates to a nanoparticle comprising a human transferrin protein and a gadolinium mineral.

In another aspect, the invention generally relates to a composition including the nanoparticles disclosed herein.

In yet another aspect, the invention generally relates to a contrast agent for magnetic resonance imaging. The contrast agent is comprised of a human transferrin protein and a gadolinium mineral.

In yet another aspect, the invention generally relates to a contrast agent composition disclosed herein.

In yet another aspect, the invention generally relates to a method for magnetic resonance imaging, comprising administering to a subject in need thereof a composition comprising the nanoparticles disclosed herein.

In yet another aspect, the invention generally relates to a method for magnetic resonance imaging, comprising administering to a subject in need thereof a composition comprising the contrast agent disclosed herein.

In yet another aspect, the invention generally relates to a method for preparing a nanoparticle, comprising reacting $Ga(NO_3)_3$ and human transferrin in a basic aqueous solution.

In yet another aspect, the invention generally relates to a method for magnetic resonance imaging and concomitant delivery of a therapeutic agent. The method includes administering to a subject in need thereof a composition comprising nanoparticles or contrast agents disclosed herein.

DETAILED DESCRIPTION OF THE INVENTION

Figure 1:
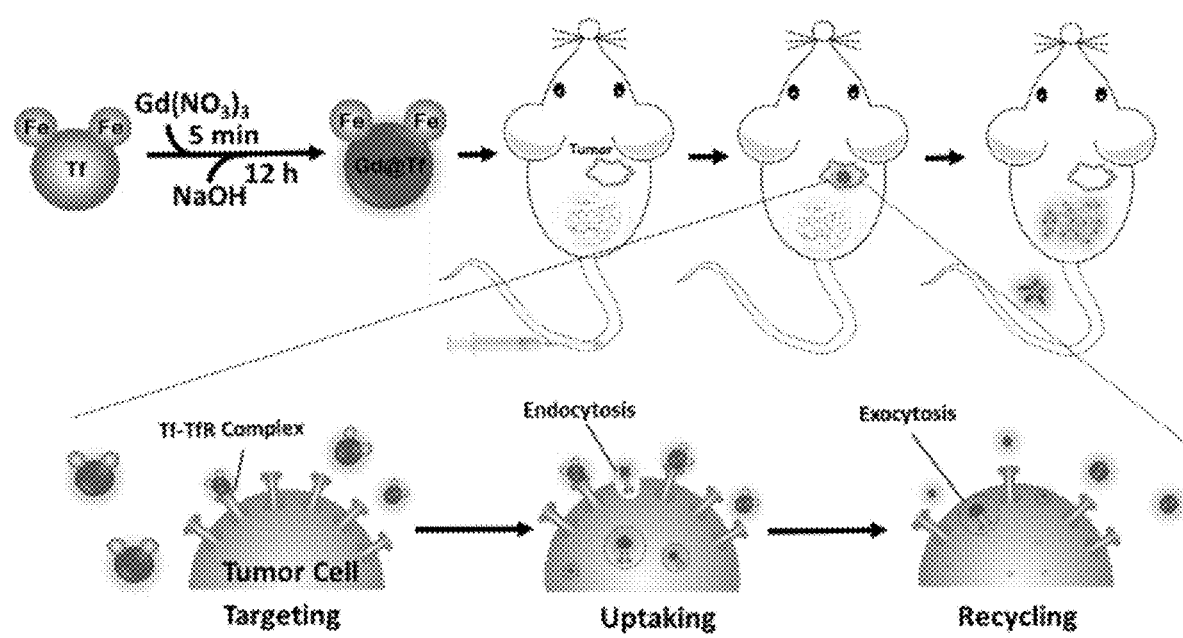
FIG. 1. Gd nanoparticles biomineralized in the template of Tf proteins. After tail vein injection, Gd@Tf NPs were accumulated in the tumor areas and finally eliminated from the body via the hepatobiliary system, demonstrating that Gd@Tf NPs are tumor targeting and metabolically clearable.

The invention is based in part of the unexpected discovery of a new class of MRI contrast agents, i.e., tumor-targeting, gadolinium biomineralized human transferrin (Tf) protein-based nanoparticles (Gd@Tf NPs).

This is believed to be the first human protein-based MRI nanoparticles with tumor targeting and outstanding clearance. It represents a new approach to biocompatible multi-functional MRI contrast agents useful for a wide range of clinical imaging and treatment applications.

More particularly, the contrast agents disclosed herein not only exhibit superior paramagnetic properties compared to conventional Gd-based contrast agents, but also maintain the normal physiological functions of the intact Tf protein, e.g., excellent biocompatibility, negligible immunogenicity, outstanding tumor-targeting and body-clearable abilities.

In human bodies, transferrin protein is an endogenous glycoprotein that plays an important role in the metabolism of iron. In particular, Tf proteins act as iron ion shuttles in Tf expressed cells. Upon binding to the transferrin receptor (TfR) on the cell surface, it can deliver iron ion payloads into cells via receptor-mediated endocytosis. After iron being released into the cytoplasm, iron-free Tf recycles back to the extracellular space. Since cancer cell proliferation leads to a great need for iron, TfR is found overexpressed in many malignancies at levels many times higher than those in normal cells, making TfR an essential target for specific recognition of tumor cells. (Hamilton, et al. *Proc. Natl. Acad. Sci. USA* 76, (12), 6406-10; Trowbridge, et al. 1981 *Proc Natl Acad Sci USA* 78, (5), 3039-43; Faulk, et al. 1980 *Lancet* 2, (8191), 390-2.)

As a natural ligand of TfR, Tf has been widely used as an additional adjuvant moiety to be conjugated to varied types of nanoparticles for the targeting of tumors. Yet, the resultant nanoparticles are much larger in size than unmodified nanoparticles and Tf alone, thus significantly altering physiological functions. (Tortorella, et al. 2014 *Curr. Drug Deliv.* 11, (4), 427-43; Chen, et al. 2017 *Colloids. Surf. B. Biointerfaces* 152, 77-84; Li, et al. 2016 *Nanoscale* 8, (37), 16662-16669; Wang, et al. 2016 *Sci Rep.* 6, 27421; Kang, et al. 2015 *J. Mol. Pharm.* 12, (8), 2947-61.)

Biocompatibility, targeting, and clearance are key challenges in the design of new MRI contrast agents. The present invention addresses these challenges by employing a gadolinium biomineralized human transferrin protein-based nanoparticle for MRI applications.

As compared to the conventional gadolinium chelates, the Gd@Tf NPs of the invention are characterized by outstanding chemical stability and superior longitudinal relaxation. Importantly, Tf protein-based MR NPs of the invention integrate T1 signal amplification, precise tumor targeting, and systematic clearance capabilities, as evidenced by MR images showing that Gd@Tf indeed retained the natural tumor targeting ability and the subsequent tumor retrieval biofunctions of Tf.

As disclosed in the examples herein, endogenous human Tf was utilized as the biotic template to fabricate Tf-based gadolinium nanoparticles via the biomineralization processes. In addition to the superior chemical and physical properties, including high T1 relaxivity and excellent stability, in vitro and in vivo results demonstrate that the prepared Gd@Tf NPs preserve the favorable intrinsic characteristics of Tf, such as biocompatibility, precise tumor-targeting, and efficient body clearance through the hepatobiliary system (FIG. 1).

Significantly, these NPs are suitable for functional modifications. As a consequence, the Gd@Tf NPs of the invention hold a great potential for a wide range of clinical applications as a promising and advanced MRI contrast agent.

In one aspect, the invention generally relates to a nanoparticle comprising a human transferrin protein and a gadolinium mineral.

In certain embodiments, the gadolinium mineral is deposited within the tertiary structural of the human transferrin protein. The human transferrin protein remains biocompatible and body-clearable and retains its tumor-targeting properties.

In certain embodiments, the gadolinium mineral is one or more selected from $Gd_2O_3$, GdOOH, GdN, $GdPO_4$, $Gd(C_2O_4)$, $GdF_3$, $Gd_2(CO_3)_3$ and Gd.

The sizes of the nanoparticles may be designed to meet specific needs. In certain embodiments, the nanoparticles have a median size from about 1 nm to about 200 nm (e.g., from about 1 nm to about 100 nm, from about 1 nm to about 70 nm, from about 1 nm to about 50 nm, from about 1 nm to about 30 nm, from about 1 nm to about 20 nm, from about 1 nm to about 10 nm, from about 5 nm to about 200 nm, from about 5 nm to about 100 nm, from about 10 nm to about 100 nm, from about 20 nm to about 100 nm, from about 30 nm to about 100 nm, from about 50 nm to about 100 nm, from about 5 nm to about 20 nm, from about 10 nm to about 50 nm).

In another aspect, the invention generally relates to a composition including the nanoparticles disclosed herein.

In yet another aspect, the invention generally relates to a contrast agent for magnetic resonance imaging. The contrast agent is comprised of a human transferrin protein and a gadolinium mineral.

In certain embodiments of the contrast agent, the gadolinium mineral is deposited within the tertiary structural of the human transferrin protein. The human transferrin protein remains biocompatible and body-clearable and retains its tumor-targeting properties.

In certain embodiments of the contrast agent, the gadolinium mineral is one or more selected from $Gd_2O_3$, GdOOH, GdN, $GdPO_4$, $Gd(C_2O_4)$, $GdF_3$, $Gd_2(CO_3)_3$ and Gd.

In certain embodiments of the contrast agent, the contrast agent is in the form of nanoparticles. The sizes of the nanoparticles may be designed to meet specific needs. In certain embodiments, the nanoparticles have a median size from about 1 nm to about 200 nm (e.g., from about 1 nm to about 100 nm, from about 1 nm to about 70 nm, from about 1 nm to about 50 nm, from about 1 nm to about 30 nm, from about 1 nm to about 20 nm, from about 1 nm to about 10 nm, from about 5 nm to about 200 nm, from about 5 nm to about 100 nm, from about 10 nm to about 100 nm, from about 20 nm to about 100 nm, from about 30 nm to about 100 nm, from about 50 nm to about 100 nm, from about 5 nm to about 20 nm, from about 10 nm to about 50 nm).

In certain embodiments, the nanoparticles of the invention are conjugated to a therapeutically active agent. In certain embodiments, the contrast agents of the invention are conjugated to a therapeutically active agent.

Any suitable therapeutic agents may be conjugated to the nanoparticles, for example, chemotherapeutic agent.

The term "chemotherapeutic agent" is a chemical compound useful in the treatment of cancer. Examples of chemotherapeutic agents include Erlotinib (TARCEVA®, Genentech/OSI Pharm.), Bortezomib (VELCADE® Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g. calicheamicin, especially calicheamicin gammaII and calicheamicin omegaII (Angew Chem. Intl. Ed. Engl. (1994) 33: 183-186); dynemicin, including dynemicin A; bisphosphonates, such as clodronate; an esperamicin; as well as neocarzinostatin chromophore and related chromoprotein enediyne antibiotic chromophores), aclacinonsins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esonibicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially 1-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE®

(Cremophor-free), albumin-engineered nanoparticle formulations of paclitaxel (American Pharmaceutical Partners, Schaumberg, 111.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

In yet another aspect, the invention generally relates to a contrast agent composition disclosed herein.

In yet another aspect, the invention generally relates to a method for magnetic resonance imaging, comprising administering to a subject in need thereof a composition comprising the nanoparticles disclosed herein.

In yet another aspect, the invention generally relates to a method for magnetic resonance imaging, comprising administering to a subject in need thereof a composition comprising the contrast agent disclosed herein.

In certain embodiments, the method further includes performing magnetic resonance imaging on the subject.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

In certain embodiments of the method, the nanoparticle or contrast agent serves as T1 MRI contrast agent. In certain embodiments of the method, the nanoparticle or contrast agent causes negligible immunogenicity.

In yet another aspect, the invention generally relates to a method for preparing a nanoparticle, comprising reacting $Ga(NO_3)_3$ and human transferrin in a basic aqueous solution.

In certain embodiments, the aqueous solution has a pH from about 7 to about 12 (e.g., from about 8 to about 12, from about 9 to about 12, from about 10 to about 12, from about 11 to about 12, from about 7 to about 11, from about 7 to about 10, from about 7 to about 9, from about 9 to about 11).

In certain embodiments, the basicity of the aqueous solution is achieved by the addition of NaOH, KOH, $Na_2CO_3$, or $NH_4OH$. In certain embodiments, the molar ratio of $Gd(NO_3)_3$ to human transferrin (Tf) is from about 5,000 to about 1 (e.g., from about 2,000 to about 1, from about 1,000 to about 1, from about 500 to about 1, from about 100 to about 1, from about 50 to about 1, from about 25 to about 1, from about 10 to about 1, about 1).

In certain embodiments, the reaction is conducted at a temperature from about 5° C. to about 70° C. (e.g., from about 5° C. to about 60° C., from about 5° C. to about 50° C., from about 5° C. to about 40° C., from about 5° C. to about 30° C., from about 10° C. to about 70° C., from about 20° C. to about 70° C., from about 30° C. to about 70° C., from about 40° C. to about 70° C.).

In certain embodiments, the method of preparation further includes purifying the resultant nanoparticles. In certain embodiments, the resulting nanoparticles have a median size from about 1 nm to about 200 nm (e.g., from about 1 nm to about 100 nm, from about 5 nm to about 100 nm, from about 5 nm to about 70 nm, from about 5 nm to about 50 nm, from about 5 nm to about 30 nm, from about 5 nm to about 20 nm, from about 5 nm to about 15 nm, from about 10 nm to about 100 nm, from about 20 nm to about 100 nm, from about 30 nm to about 100 nm, from about 50 nm to about 100 nm, from about 10 nm to about 20 nm, from about 10 nm to about 50 nm).

In yet another aspect, the invention generally relates to a method for magnetic resonance imaging and concomitant delivery of a therapeutic agent. The method includes administering to a subject in need thereof a composition comprising nanoparticles or contrast agents disclosed herein.

In certain embodiments, the method further includes performing magnetic resonance imaging on the subject.

The following examples are meant to be illustrative of the practice of the invention and not limiting in any way.

EXAMPLES

In the biomineralization approach, aqueous gadolinium nitrate solution was added into a Tf solution. Subsequently, NaOH was introduced to allow the formation of $Gd_2O_3$ and simultaneously unfold Tf, which promoted the precipitation of $Gd_2O_3$ nanoparticles into Tf. The final Gd@Tf NPs were obtained as a clean, transparent and stable solution. However, in the absence of a protein scaffold, $Gd_2O_3$ molecules aggregated to form large insoluble particles, which made the final product cloudy. These results showed that Tf could function as an efficient template for the growth of Gd-based nanoparticles. In this synthetic process, the Tf could significantly influence the chemical properties of $Gd_2O_3$ molecules and reduce the undesired precipitate. These results demonstrated that biomineralization changed the synthetic process of $Gd_2O_3$ nanoparticles.

Figure 5:
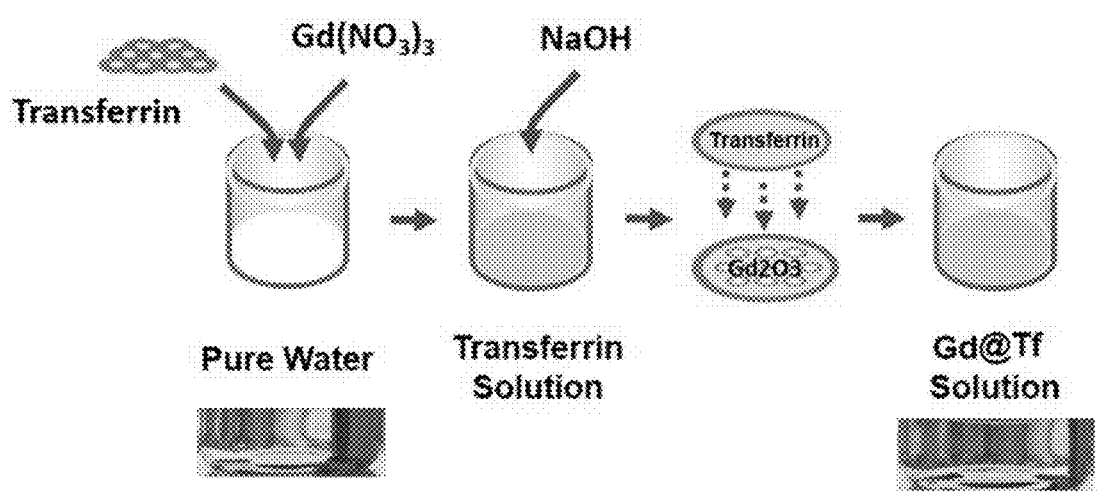
FIG. 5. Synthesis of $Gd_2O_3$ nanoparticles with (a) or without (b) the Tf-protein template.
Figure 5:
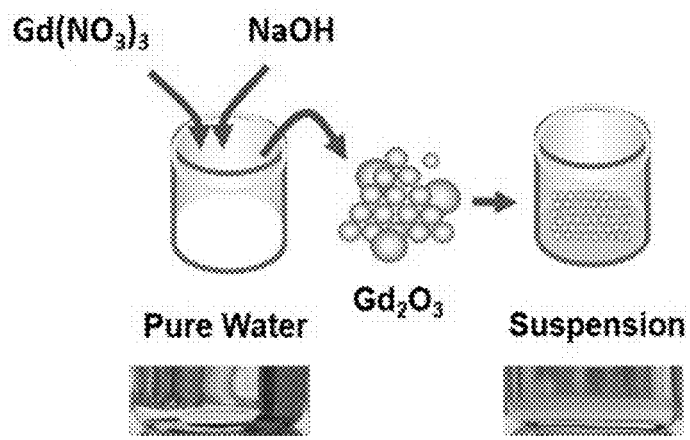

The Gd@Tf NPs were prepared by mimicking the natural biomineralization process. In brief, 2.7 mg of $Gd(NO_3)_3$ and 30 mg of Tf were dissolved in 1.2 mL of pure water at 37° C. and stirred for 5 min. Then, 0.06 mL of NaOH (1 M) was added to the mixture and the subsequent solution was stirred for 12 h at 37° C. After purification, the final Gd@Tf NPs were obtained as a transparent solution (FIG. 5).

Figure 6:
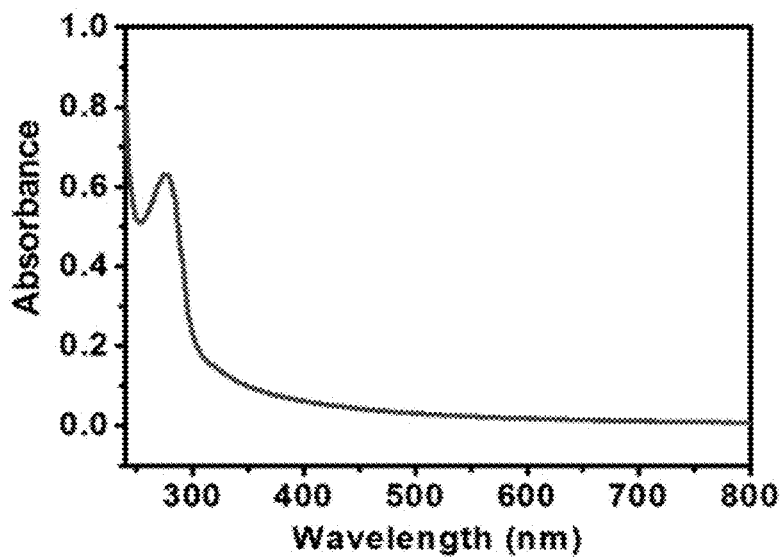
FIG. 6. The UV-VIS absorption spectrum of the prepared Gd@Tf NPs.

An absorption peak was found at 280 nm of UV-VIS absorbance spectroscopy, corresponding to the characteristic absorption of proteins. This result confirmed the presence of the protein component in the Gd@Tf NPs (FIG. 6).

Figure 2:
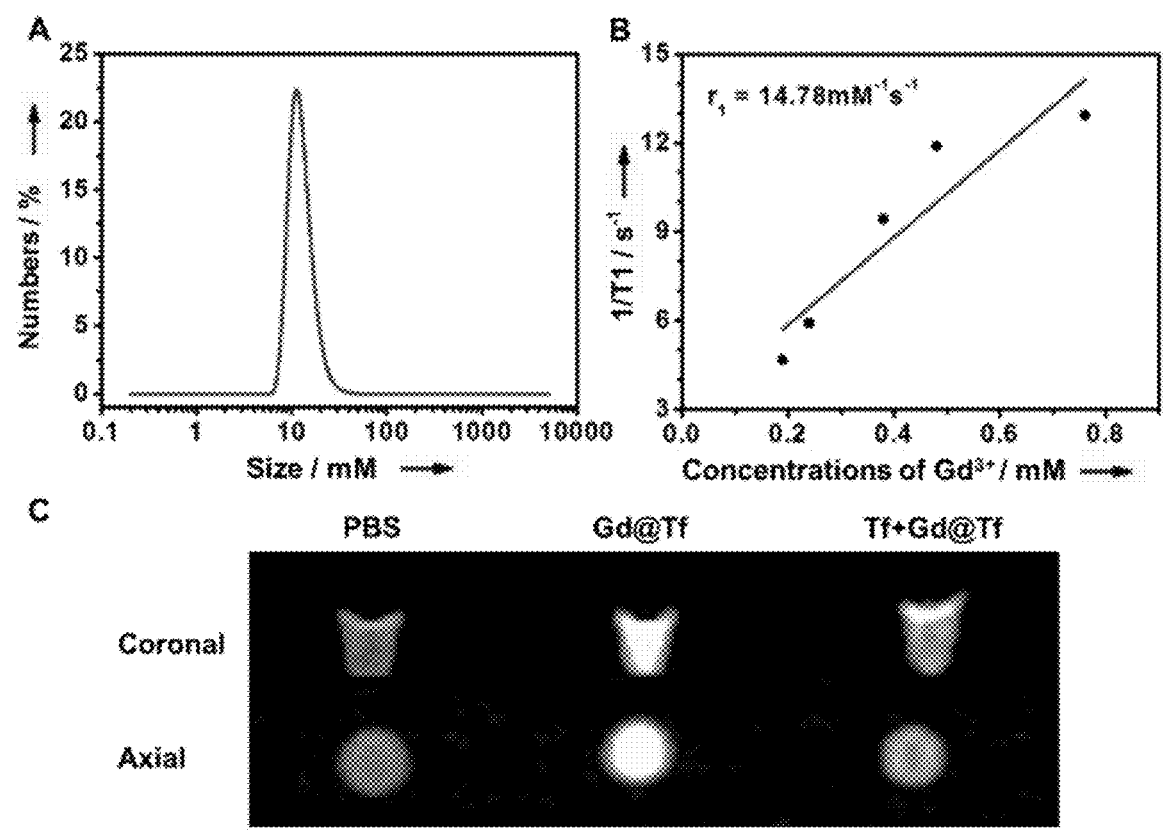
FIG. 2. (a) Hydrodynamic size distributions and (b) rl relaxivity curve for Gd@Tf NP. (c) In vitro T1-weighted MR images of PC-3 cell suspensions after treatment of phosphate-buffered saline (PBS), Gd@Tf NPs, and Tf+Gd@Tf NPs. The signal intensity of PC-3 cells, which were treated by excess Tf followed by Gd@Tf NPs, were found to be significantly lower than those subjected only to Gd@TfNPs.
Figure 7:
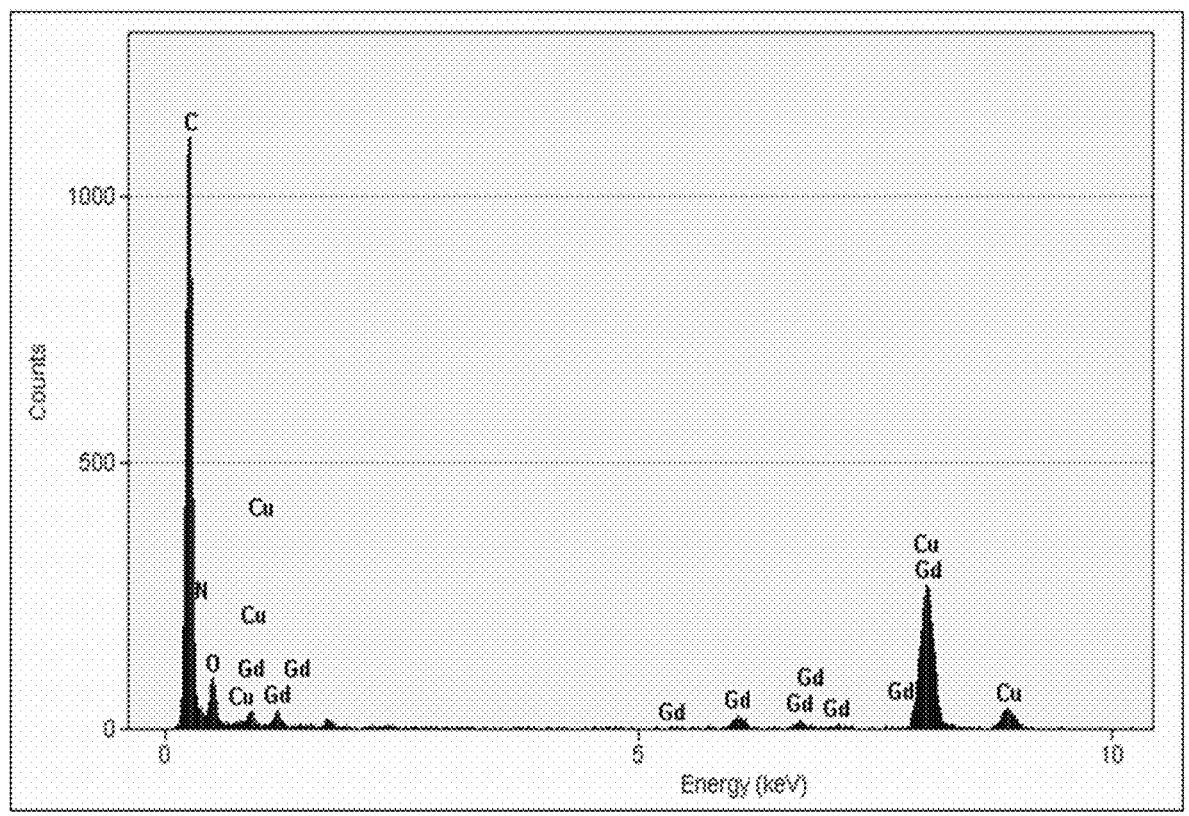
FIG. 7. EDX spectrum graph of the prepared Gd@Tf NPs.
Figure 8:
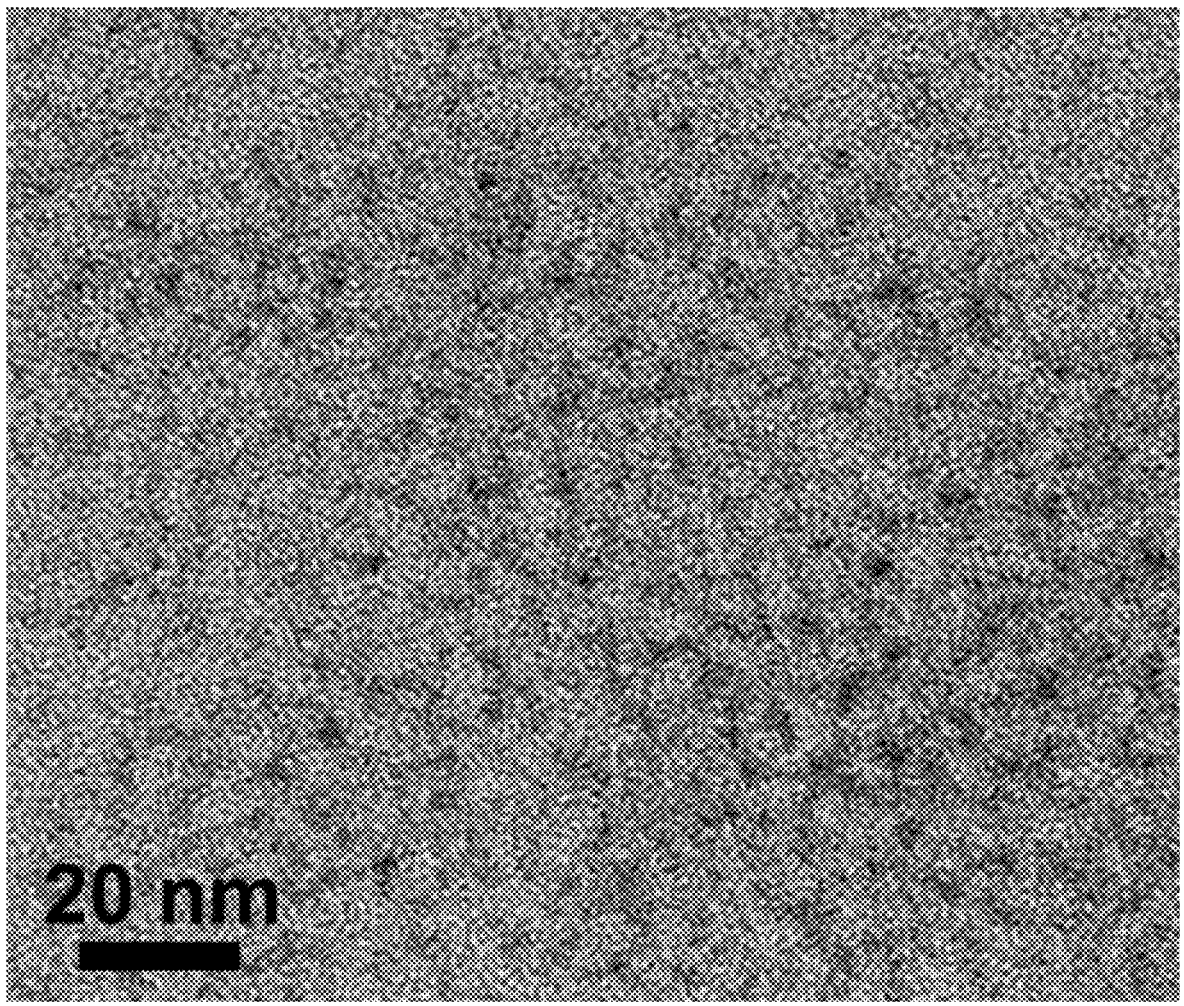
FIG. 8. HRTEM image presents an ultrasmall and uniform nanoparticle with a diameter about 2-3 nm.

The average hydrodynamic diameter of Gd@Tf NPs was determined as approximately 9 nm by dynamic light scattering (DLS; FIG. 2A). The zeta-potential of Tf showed no obvious change (from −8.73 mV to −6.27 mV) after the reaction. Moreover, energy dispersive X-ray (EDX) spectroscopy studies (FIG. 7) indicated that the formation of $Gd_2O_3$ was within the Tf-protein template. Transmission electron microscopy (TEM; FIG. 8) images revealed that the encapsulated $Gd_2O_3$ was approximately 2-3 nm in diameter.

In order to demonstrate the paramagnetic capacity of Gd@Tf NPs, the T1 relaxivity was determined by the slope of the 1/T1 (R1) plot versus the Gd(III) ion concentration (FIG. 2B). Our Gd@Tf NPs (14.78 $mM^{-1}$ $s^{-1}$, FIG. 2B) were found to have much higher T1 relaxivity than that of commercial MRI contrast agent Magnevist (3-5 $mM^{-1}$ $s^{-1}$). (Park, et al. 2009 *ACS Nano* 3, (11), 3663-9.)

Figure 9:
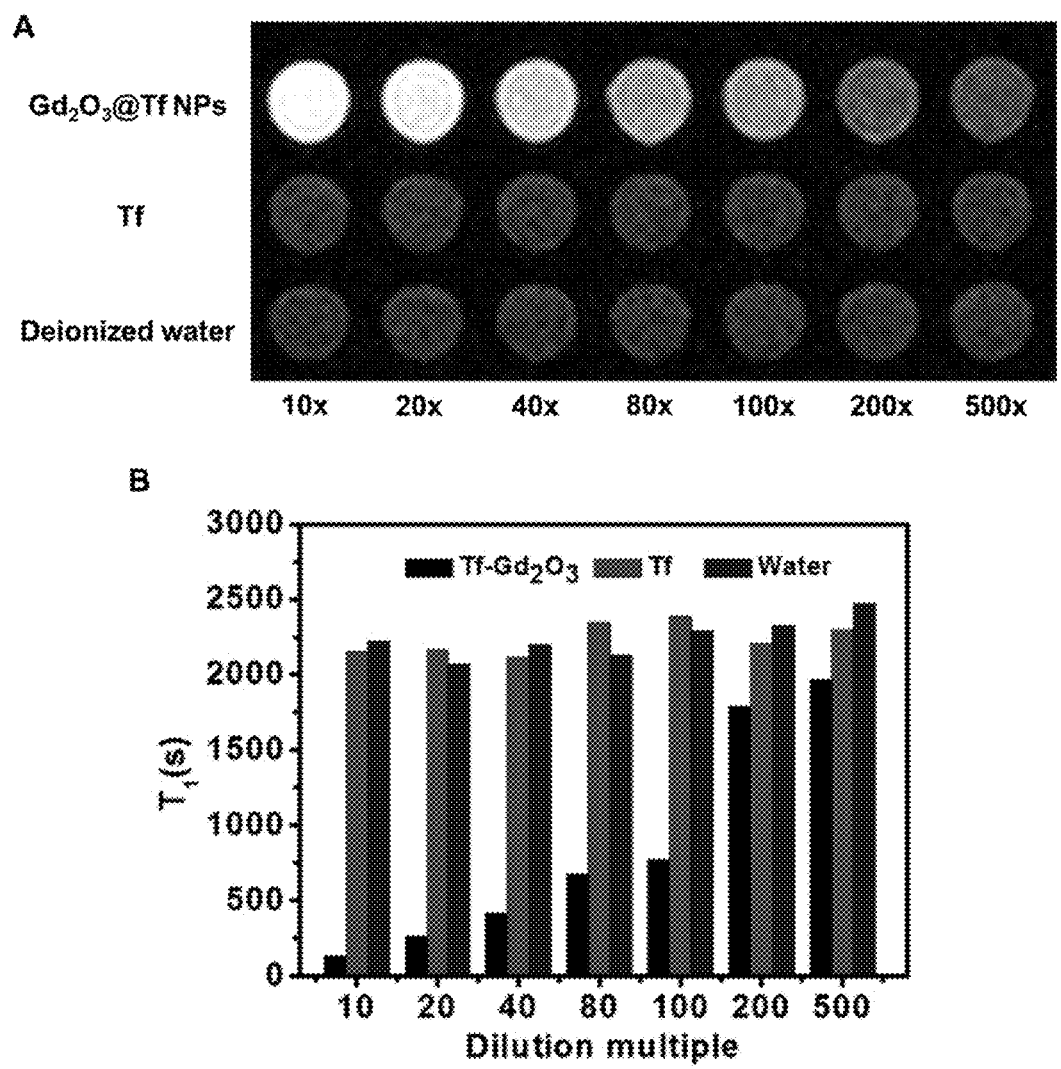
FIG. 9. The T1-weighted MR images (a) and their longitudinal relaxation time (T1, b) of Gd@Tf NPs, Tf and deionized water after their stock solutions were diluted into various times (from 10 to 500). The initial solution of Gd@Tf NPs contained 3.815 mM Gd. Tf content in the protein stock solution was the same as that of Gd@Tf NPs stock solution.

This phenomenon occurred because the relaxivity of metal ions could be increased after binding with proteins. Gd@Tf NPs solutions also exhibited an obvious dose-dependent brightening effect on the T1-weighted MR images; whereas Tf solutions and deionized water triggered no changes in signal intensity at various concentrations (FIG. 9). This result demonstrated that Gd@Tf NPs shortened T1 times, but Tf solutions and deionized water had no similar functions.

Figure 10:
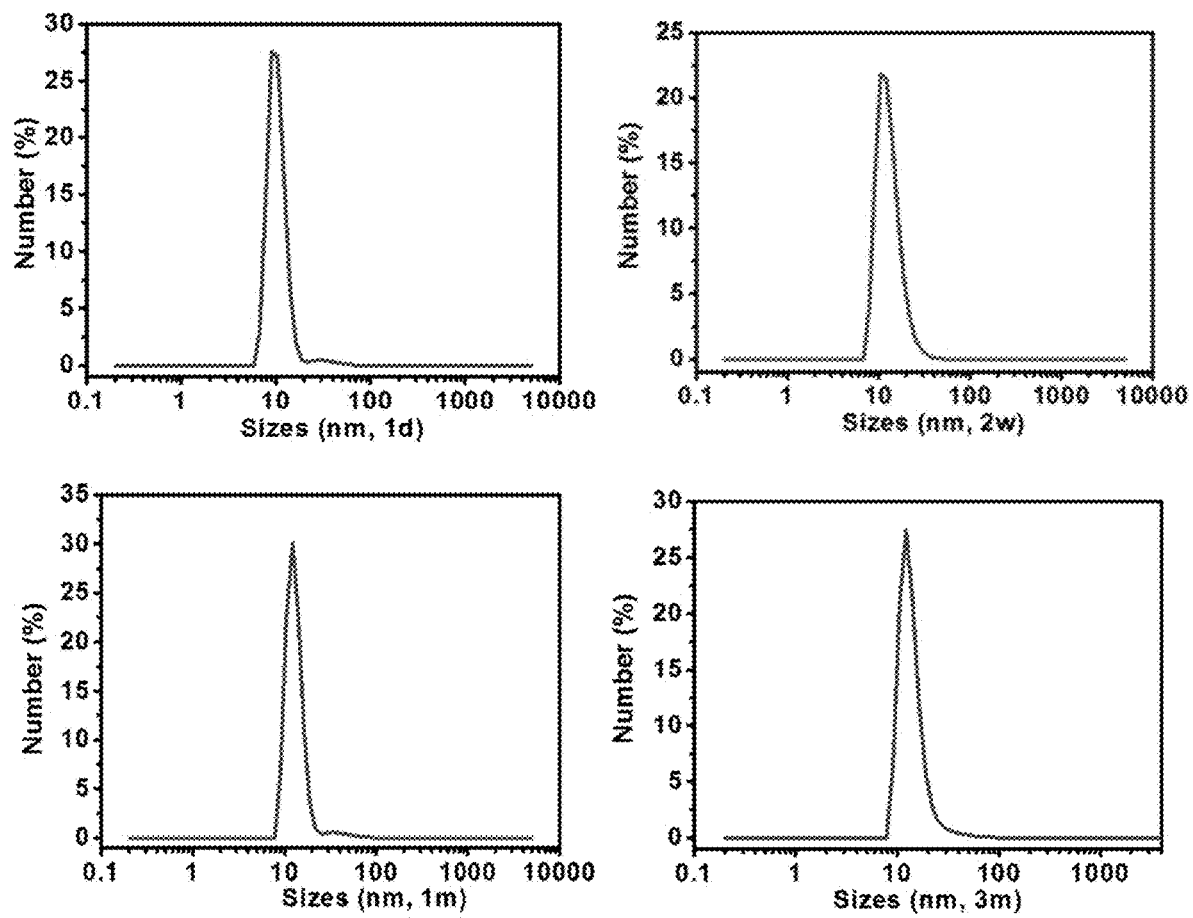
FIG. 10. The hydrodynamic diameter of Gd@Tf NPs in PBS measured by DLS after storage of 1 day, 2 weeks, 1 month and 3 months at 4° C.

Following storage in PBS for 3 months at 4° C., excellent dispersion stabilities were observed in the prepared Gd@Tf NPs with respect to their colloidal and magnetic properties, benefiting the end use and storage. No significant aggregations or noticeable changes in hydrodynamic sizes were observed in the dispersion samples, indicating the exceptional dispersion stability of the prepared Gd@Tf NPs (FIG. 10).

Figure 11:
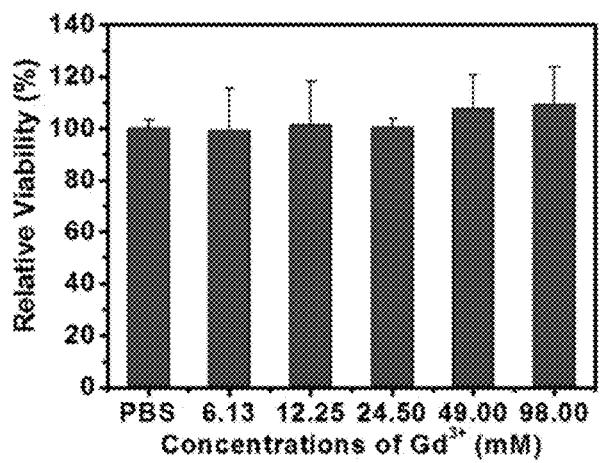
FIG. 11. Relative viabilities of PC-3 cell lines after incubation with different concentrations of Gd@Tf NPs for 24 h.

These results demonstrated that the prepared Gd@Tf NPs are superior T1 MRI contrast agent candidates due to their ultra-small size of $Gd_2O_3$ within the protein, high T1 enhancement effects and good stability. To further test their potential for biomedical applications, the cytotoxicity of Gd@Tf NPs was then evaluated by methyl thiazolyltetrazolium (MTT) assay. It was found that PC-3 cell viabilities were not influenced by Gd@Tf NPs, even at high doses of Gd of up to 98 μM (FIG. 11). These results showed that the template of Tf offers great biocompatibility to Gd-based Tf NPs, which is essential with respect to applications of Gd@Tf NPs.

Next, the cellular uptake of Gd@Tf NPs was investigated by T1-weighted MRI. The treatment of Gd@Tf NPs resulted in a remarkable increase in T1 signal intensity within PC-3 cells relative to cells treated with PBS, indicating that Gd@Tf NPs were able to be efficiently internalized by cancer cells (FIG. 2C).

Figure 12:
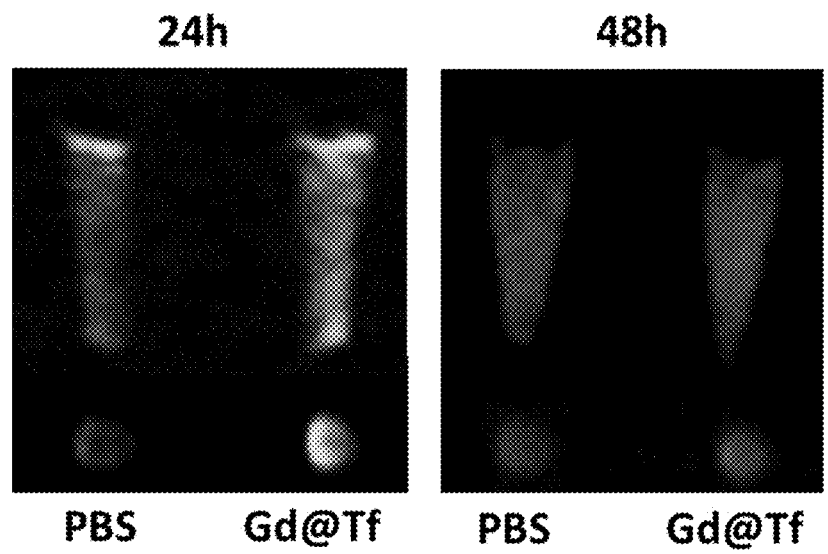
FIG. 12. T1 MR imaging of PC-3 cells after they were incubated with Gd@TfNPs or PBS, rinsed in distilled water, and resuspended in centrifuge tubes.

It was found that, like the Tf proteins, Gd@Tf NPs may be shuttled out of the treated cells, as their signal intensity in cells decreased over time (FIG. 12). After a 24 h incubation, a significantly positive enhancement effect was observed in tumor cells treated with Gd@Tf NPs compared with the PBS-treated cells, demonstrating the efficient uptake of Gd@Tf NPs by tumor cells. However, tumor cells treated with Gd@Tf NPs for 48 h revealed similar T1 signal to the PBS-treated group, indicating that the prepared Gd-based NPs could reversibly recycle back to the extracellular space following the exocytosis of Tf. Therefore, Tf proteins could act as a promising shuttle that transfers Gd-based NPs into and out of Tf expressed cells. Competition experiments were further performed to evaluate whether Tf of Gd@Tf NPs preserved their biological functions to specifically bind to TfRs, and thus mediate endocytosis of Gd@Tf NPs through Tf-TfR interactions.

FIG. 13(a) shows competition inhibition experiments with natural Tf proteins. After incubating PC-3 cells with excess Tf proteins, TfR overexpressed on the membrane of tumor cells, could be specifically blocked by these unlabeled Tf, thus preventing the uptake of Gd@Tf NPs into tumor cells via the TfR-mediated endocytosis. FIG. 13(b) shows signal intensity of PC-3 cells suspensions after the treatment of PBS, Gd@Tf NPs and Tf+Gd@Tf NPs, respectively. In comparison with tumor cells only subjected to Gd@Tf NPs, pretreatment with excess Tf led to significantly decreased signal intensity in PC-3 cells with subsequent incubation with Gd@Tf NPs.

Figure 13:
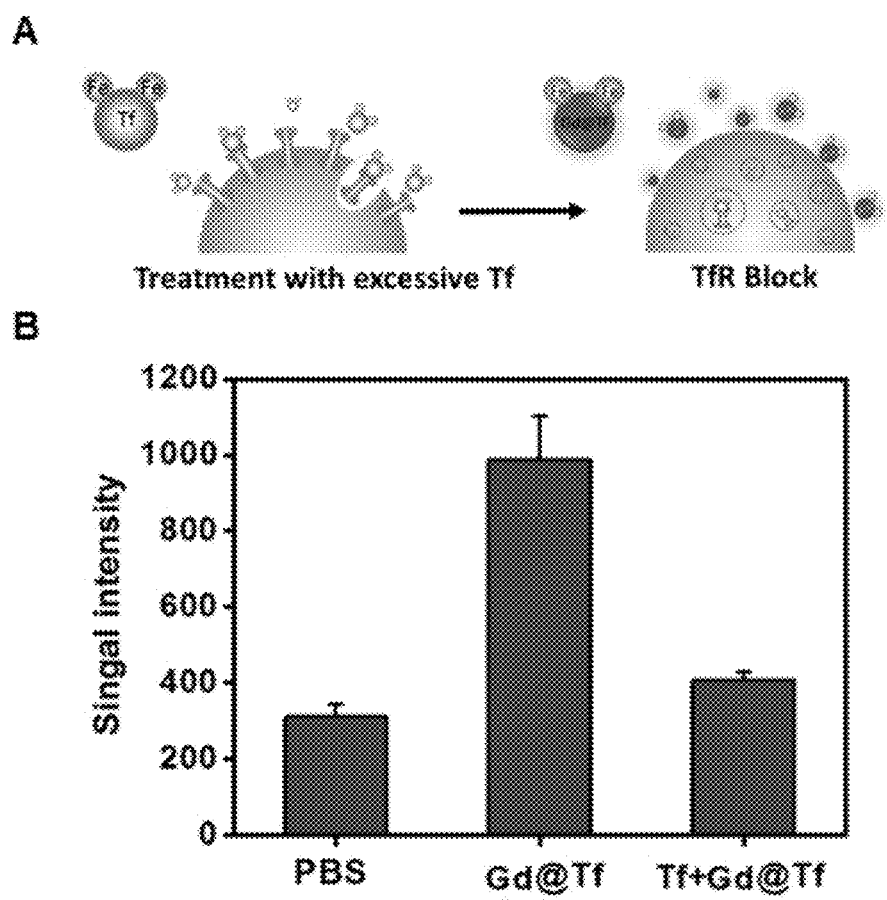
FIG. 13. (a) Schematic illustration for competition inhibition experiments with natural Tf proteins. (b) Signal intensity of PC-3 cells suspensions after the treatment of PBS, Gd@Tf NPs and Tf+Gd@Tf NPs, respectively.

The pre-treatment of Tf protein only lead to a significant decrease in signal intensity on T1 weighted imaging, which indicates that Tf protein indeed blocked binding sites for Gd@Tf NPs and inhibit endocytosis of Gd@Tf NPs into tumor cells (FIGS. 2C and 13). As a result, the cellular uptake of Gd@Tf NPs was mainly dependent on active targeting mechanisms mediated by the Tf-TfR delivery system. The biomineralization process did not interfere with the natural cell targeting and shuttle functions of Tf in Gd@Tf NPs.

Figure 3:
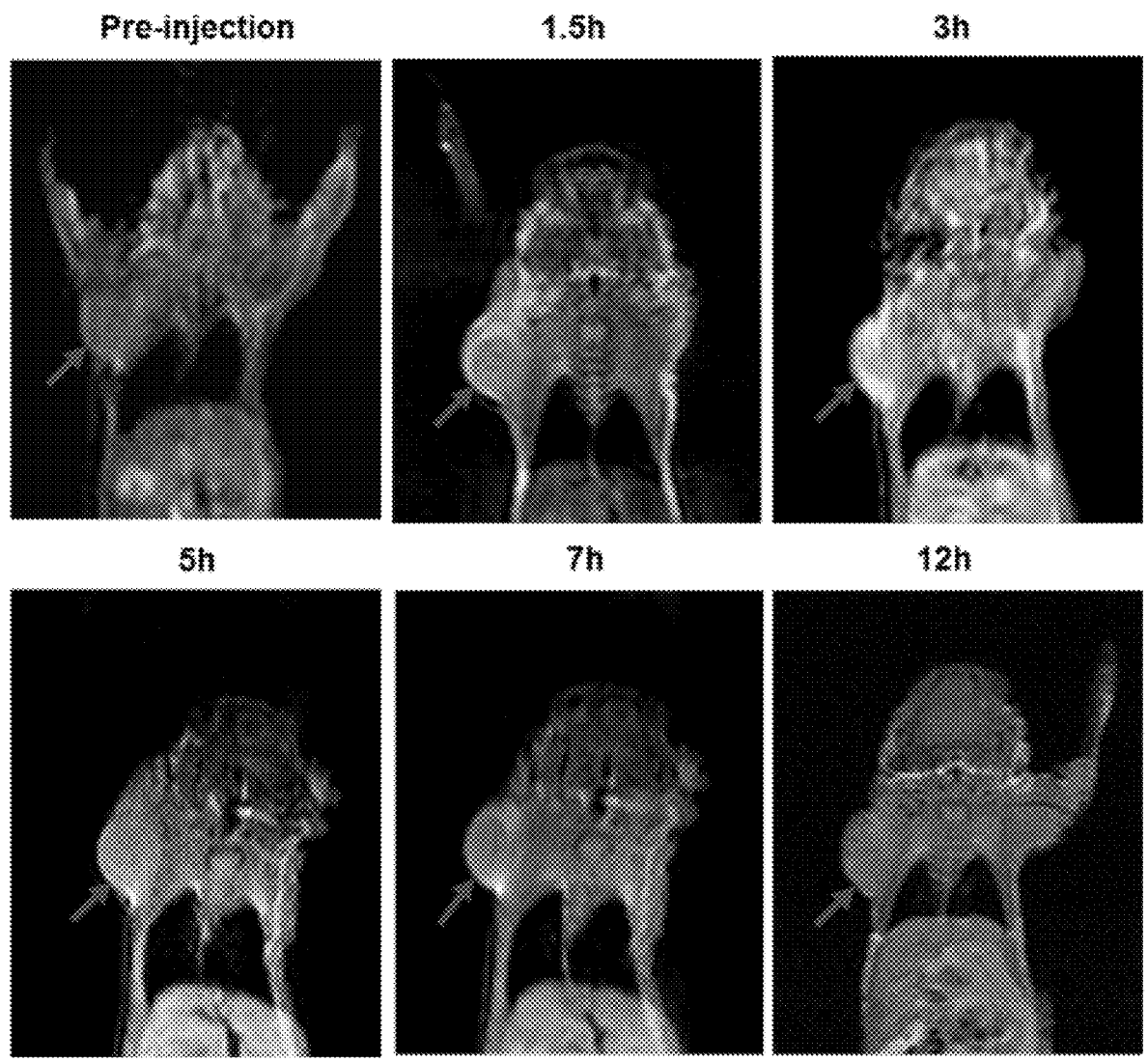
FIG. 3. In vivo T1-weighted MR images of PC-3 tumors before and after intravenous injection of Gd@Tf NPs. Significant signal enhancement was observed in the tumors (red arrows) and reached its maximum point at about 3 h post injection. After 3 h, the MR signal gradually descended from the central portion of the tumor region.

To further evaluate the in vivo performance of Gd@Tf NPs, a series of in vivo MRI was carried out. After tail-vein injection of Gd@Tf NPs, the tumor regions showed strong MR signal enhancement (FIG. 3) as a result of the targeted accumulation of Gd@Tf NPs through targeting mechanisms of Tf-TfR.

Figure 14:
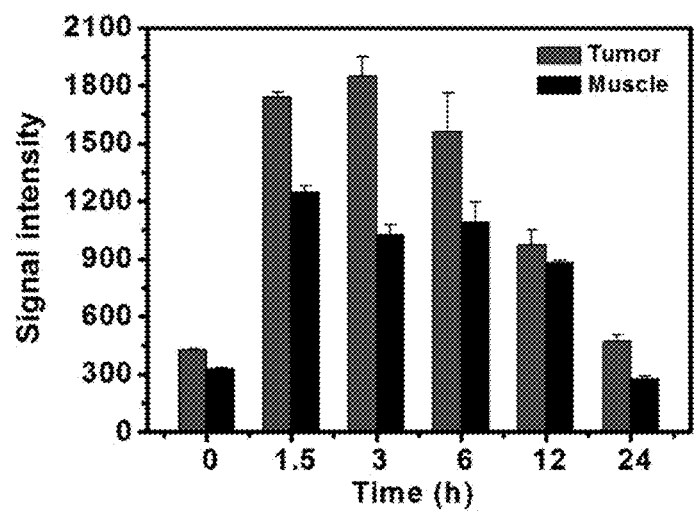
FIG. 14. Signal intensity of tumor and muscle measured on the T1 MR images at various time points after vein injection of Gd@Tf NPs.

The T1 signal intensity in the tumors post injection relative to the baseline was measured. The obvious enhancement effect appeared in the tumor areas at 1.5 h post injection, with maximum signal intensity at the 3 h time point (FIG. 14). Such high contrast enhancement makes tumors clearly distinguishable from the surrounding tissues. Similar to the process of $Fe^{3+}$ transport by Tf in physiological reactions, Gd@Tf NPs were rapidly taken up into and efficiently excreted from tumor cells. Thus, after the peak time, MR signal intensity in tumor tissues gradually decreased from their central regions and finally returned to the baseline level.

In order to ensure biosafety for further clinical translation, it is important to evaluate the bio-clearance and the metabolism of magnetic nanoparticles after systematic administration. The dynamic MR signal transformation of metabolic organs was carefully monitored to provide a real-time visualization of the Gd@Tf metabolism.

Figure 4:
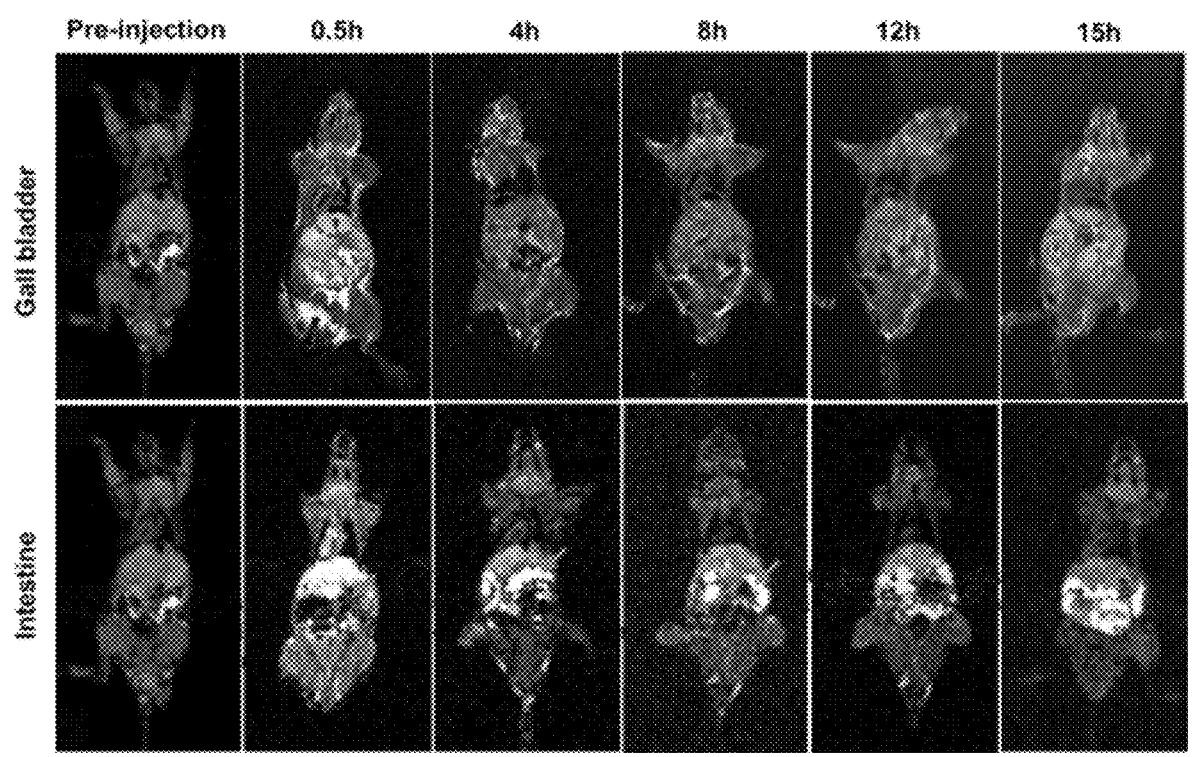
FIG. 4. In vivo T1-weighted MR images of a gall bladder section (red circles) and an intestine section (blue arrows) in PC-3 tumor-bearing mice after the intravenous injection of Gd@Tf NPs.

At baseline, the gall bladder and liver showed hypointensity like that of water and isointensity as soft tissue on T1WI, respectively. Thirty minutes after injection, the T1 signal of liver increased, while little change was observed in the signal intensity of the gall bladder. At 4 h post-injection, the gall bladder began to demonstrate a heterogeneous hyperintensity. Subsequently, its T1 signal gradually increased, and a very bright gall bladder was then detectable on T1WI from 8 h to 15 h, significantly different from the images before 0.5 h. (FIG. 4.) The T1 signal of intestines was subsequently investigated. No obvious change was found in intestinal during the first hour post-injection. At 4 h, part of the intestine began to brighten and then the hyperintense area in the enteric tract gradually expanded, clearly outlining the entire intestinal shape at 15 h post-injection.

Figure 16:
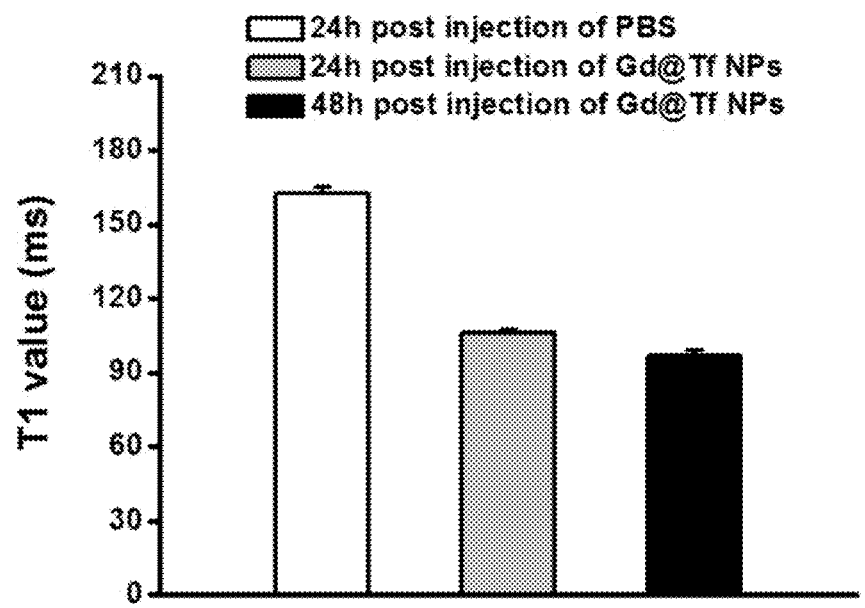
FIG. 16. The T1 values of mice feces measured by inversion-recovery MR imaging.

Furthermore, feces of all of the mice were collected during the first 2 days after injection. Feces of mice that were intravenously injected with Gd@Tf NPs for 24 h (105.99±1.38) or 48 h (97.01±1.99) exhibited shorter longitudinal relaxation times than those treated with PBS (162.73±2.33). Short T1 values appeared hyperintensity on T1-weighted images (FIG. 16). The results confirmed the presence of Gd elements in mice feces, indicating that the Gd@Tf NPs were metabolized and removed from the body through the hepatobiliary system. The T1-value analysis revealed the obvious shorter longitudinal relaxation time of the feces in the Gd@Tf NPs-treated group than that of the PBS-treated group, demonstrating that Gd@Tf being excreted out of the body with animal waste.

Figure 15:
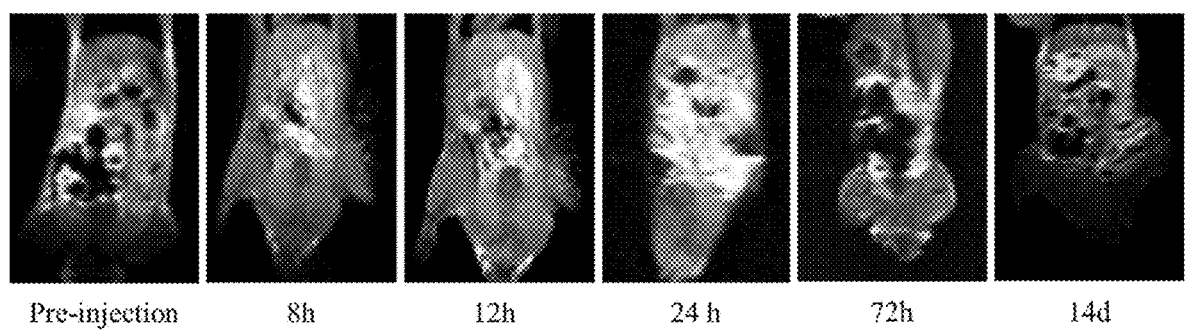
FIG. 15. In vivo T1-weighted MR images of the abdomen of PC-3 tumor-bearing mice.

Finally, the MRI findings after 14 days showed that the T1 signal of intensity had nearly come back to the baseline level. The significant signal enhancement was observed in the intestine within 24 h post-injection of Gd@Tf NPs. Following the excretion of Gd in the feces, the signal intensity gradually decreased over time, and finally returned to the baseline level at two weeks post-injection. (FIG. 15).

These results suggested the metabolic process of the Gd@Tf NPs is similar to intact Tf. They were cleared by the hepatobiliary systems and the following elimination with normal intestinal tract movement. On the other hand, unlike nanoparticles smaller than 6 nm in diameter (e.g., Gd-chelates and Au nanoclusters). No significant changes of MR signal were observed in kidneys. Without being bound to the theory, it is believed that the phenomenon is likely due to the fact that the hydrodynamic diameter of Gd@Tf NPs 5 nm) exceeds the size threshold of glomerular filtration membranes (4.5-5 nm) and is not capable of renal clearance. (Longmire, et al. 2008 *Nanomedicine* (*Lond*). 3, (5), 703-717; Grenier, et al. 2008 *Semin. Nucl. Med.* 38, (1), 47-55; Yu, et al. 2016 *Angew Chem Int Ed Engl.* 55, (8), 2787-91; Ohlson, et al. 2001 *Am. J. Physiol. Renal Physiol.* 280, (3), F396-405.)

Figure 17:
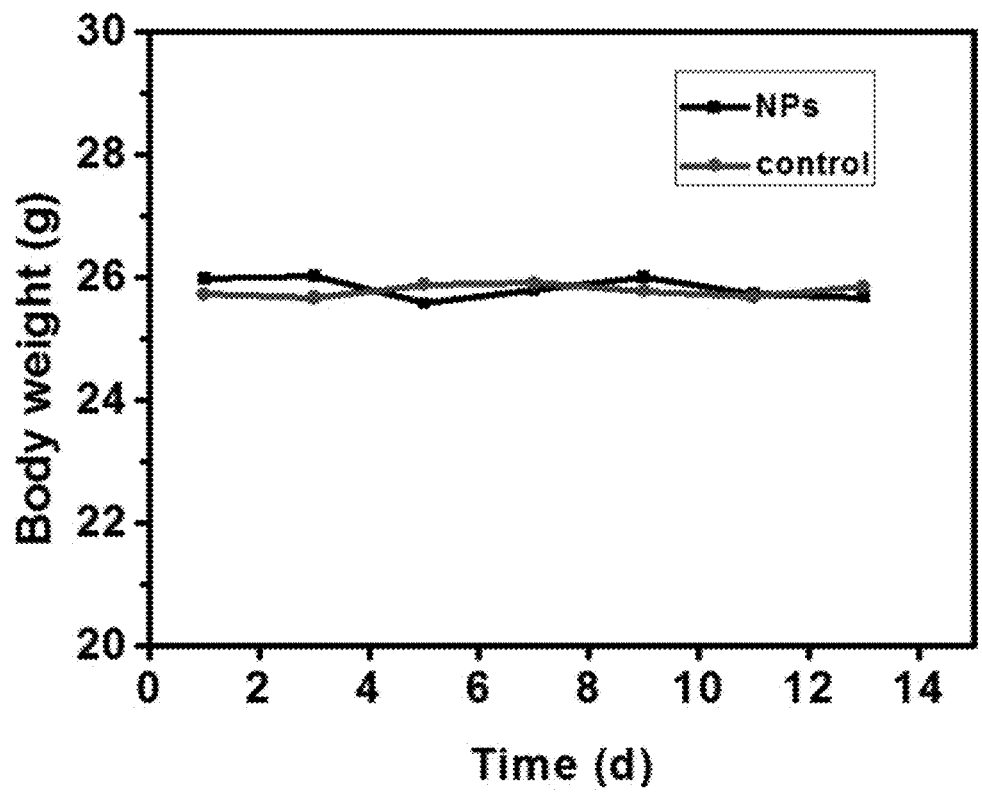
FIG. 17. Body weight changes of mice during an observational period of 2-week in the experimental and control group, which were treated by equal volumes of Gd@Tf NPs solutions and PBS, respectively.

In order to investigate the in vivo toxicity of Gd@Tf, body weight and histological changes were also evaluated. No obvious body weight loss was observed in the mice 2 weeks after the intravenous injection of Gd@Tf NPs (FIG. 17).

Figure 18:
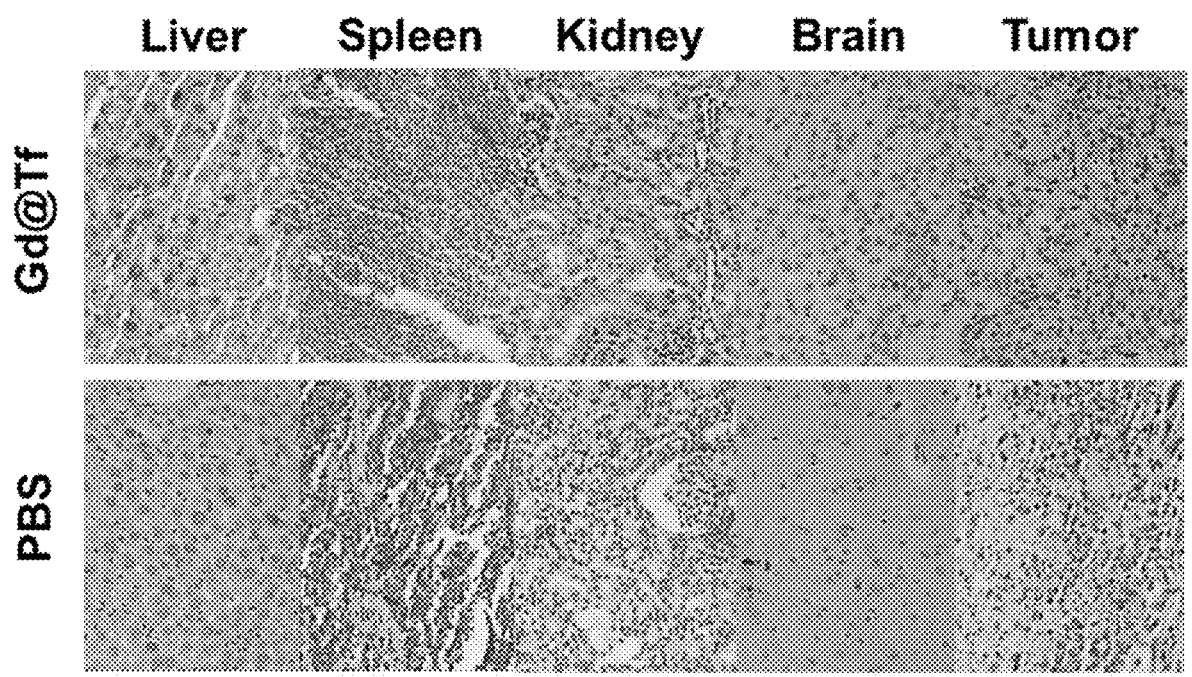
FIG. 18. Hematoxylin and eosin stained tissue sections of the main visceral organs in tumor-bearing mice two weeks post-injection of Gd@Tf NPs. Another group treated with PBS was used as a control. Magnification 10×.

No morphological changes were observed in the organs studied in relation to the treated mice, demonstrating good biocompatibility of Gd@Tf NPs (FIG. 18). The blood examinations also revealed that the essential hematological parameters were normal after treatment with Gd@Tf NPs for 14 days (Table 1), demonstrating their negligible immunogenicity.

Figure 19:
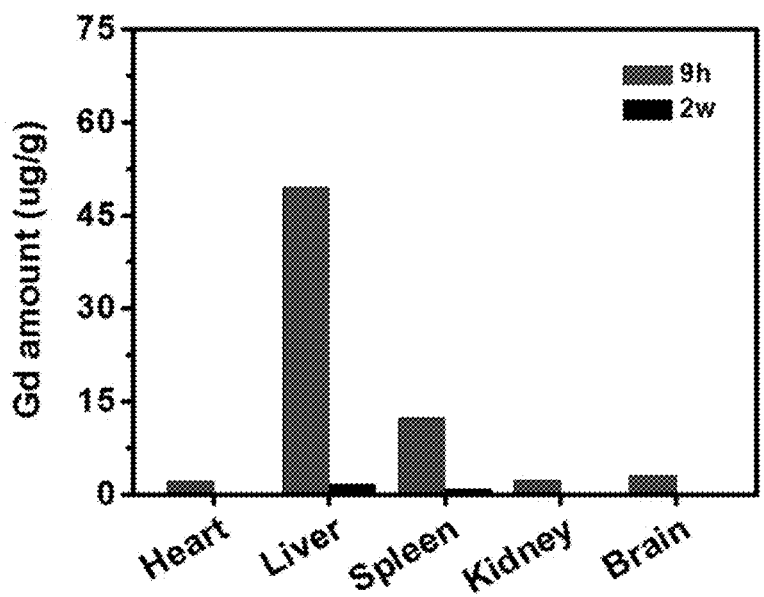
FIG. 19. Bio-distribution of Gd@Tf NPs in major organs as determined by Gd analysis by ICP-MS.

In addition, Gd content in major organs was determined by ICP-MS analysis. No obvious Gd was found to have retained in the vital organs after completion of the main metabolic processes. The highest concentration of Gd@Tf NPs was taken up by the reticuloendothelial system, whereas few Gd@Tf NPs accumulated in the heart, kidney, and brain after 9 h. After 2 weeks, the vast majority of Gd@Tf NPs had been eliminated from the body (FIG. 19). Consequently, the above results clearly confirmed the low in vivo toxicity of Gd@Tf NPs.

In Table 1, another group of mice injected with PBS were used as control. As shown, all the parameters such as WBC, RBC, HGB, PLT, HCT, MCV, MCH, and MCHC, are within the normal range after treatment with Gd@Tf NPs or PBS, demonstrating the negligible immunogenicity of Gd@Tf NPs to mice.

retained the inherent biological functions of Tf protein (e.g., biocompatibility, tumor targeting and systematic clearable abilities) and the high paramagnetic property of Gd within a single nanoplatform. The MR Gd@Tf NPs also demonstrated unique advantages over conventional nanoparticles, such as having an ultra-small size and enhanced T1 MR signal amplification. In particular, these properties resulted in high-performing Gd@Tf NPs that showed selective MRI and precise tumor localization in vivo. In addition, the protein-based MRI contrast agents were efficiently cleared by the hepatobiliary system. These results showed that Gd@Tf NPs are suitable for clinical implementation for activated and sensitive MR detection of early detection of tumor malignancy. Furthermore, the preserved tumor shuttle-like feature of Tf in such nanoparticles also enables the prepared NPs to serve as an MRI-imaging guided drug delivery vehicle for a wide range of theranostic applications.

Experimental

Materials and Chemicals

Human Tf (molecular weights 76-81 KD), Gd(NO$_3$)$_3$.6H$_2$O, and NaOH were purchased from Sigma-Aldrich (St. Louis, Mo., USA) at analytical grade or above. MTT stock solution was obtained from Amrseco (Solon, Ohio, USA). All chemicals were used as received without further purification.

Synthesis of Gd@Tf NPs

Bioinspired Tf protein was used as the template to assist the fabrication of Gd-based NPs (FIGS. 1A and S1A). Gd(NO$_3$)$_3$ (5.4 mg) and Tf (20 mg) were dissolved in pure water (1.2 mL) at 37° C. and stirred for 5 min. NaOH (1 M, 0.12 mL) was added to the mixture to induce the formation of Gd$_2$O$_3$ and simultaneously unfold Tf, which resulted in precipitation of Gd$_2$O$_3$ nanoparticles into Tf. The reaction solution was then stirred at 37° C. for 12 h. The resulting Gd@Tf NPs were washed with PBS and separated by centrifugation at 10,000 rpm for 30 min to obtain a transparent supernatant. Ultrafiltration was also performed with 30 KDa centrifugal filter unit (Amicon Ultra-15 Centrifugal

TABLE 1

Blood routine examination of mice before and after intravenous injections with Gd@Tf NPs

| | Normal Range | Control | 1 h | 6 h | 12 h | 24 h | 2 d | 4 d | 7 d | 14 d |
|---|---|---|---|---|---|---|---|---|---|---|
| WBC (K/µL) | 1.8-10.7 | 5.56 | 3.56 | 5.82 | 5.98 | 5.66 | 4.54 | 4.56 | 3.92 | 2.24 |
| NE (K/µL) | 0.1-2.4 | 0.52 | 0.95 | 1.44 | 1.50 | 0.83 | 0.87 | 1.07 | 1.23 | 0.40 |
| LY (K/µL) | 0.9-9.3 | 1.31 | 2.03 | 3.11 | 3.50 | 4.75 | 3.31 | 3.24 | 2.47 | 1.72 |
| MO (K/µL) | 0.0-0.4 | 0.01 | 0.24 | 0.58 | 0.31 | 0.03 | 0.23 | 0.11 | 0.15 | 0.11 |
| EO (K/µL) | 0.0-0.2 | 0.02 | 0.13 | 0.15 | 0.18 | 0.04 | 0.10 | 0.10 | 0.05 | 0.01 |
| BA (K/µL) | 0.0-0.2 | 0.00 | 0.09 | 0.24 | 0.18 | 0.02 | 0.03 | 0.04 | 0.02 | 0.00 |
| RBC (M/µL) | 6.36-9.42 | 9.24 | 7.48 | 7.35 | 8.72 | 9.54 | 7.15 | 8.53 | 8.1 | 7.40 |
| HGB (g/dL) | 11.0-15.1 | 11.3 | 10.8 | 12.0 | 11.1 | 15.7 | 10.7 | 13.0 | 12.3 | 12.0 |
| HCT (%) | 35.1-45.4 | 38.1 | 45.0 | 40.5 | 47.2 | 41.1 | 37.4 | 37.3 | 44.4 | 39.1 |
| MCV (fL) | 45.4-60.3 | 51.7 | 60.1 | 55.1 | 54.5 | 53.6 | 52.3 | 55.4 | 54.8 | 52.9 |
| MCH (pg) | 14.1-19.3 | 15.3 | 18.0 | 20.4 | 18.7 | 16.5 | 15.0 | 15.2 | 15.2 | 16.2 |
| MCHC (K/µL) | 30.2-34.2 | 29.5 | 30.1 | 37.0 | 33.9 | 30.7 | 29.6 | 30.7 | 30.7 | 30.7 |
| RDW (K/µL) | 12.4-27.0 | 20.6 | 21.9 | 26.7 | 28.1 | 22.5 | 20.6 | 20.7 | 18.3 | 18.1 |
| PLT (K/µL) | 592-2972 | 918 | 1094 | 1051 | 758 | 812 | 675 | 642 | 862 | 993 |
| MPV (fL) | 5.0-20.0 | 6.2 | 6.5 | 5.7 | 5.1 | 6.1 | 6.2 | 6.1 | 6.3 | 5.2 |

White blood cell (WBC), Neutrophils (NE), Lymphocytes (LY), Monocytes (MO), Eosinophils (EO), Basophils (BA), Red blood cell (RBC), Hemoglobin (HGB), Hematocrit (HCT), Mean corpuscular volume (MCV), Mean corpuscular hemoglobin (MCH), Mean corpuscular hemoglobin concentration (MCHC), Red blood cell distribution width (RDW), Platelet Thrombocyte (PLT), Mean platelet volume (MPV).

In summary, tumor-targeting and systematic clearable gadolinium-Tf NPs were successfully synthesized by a straightforward, one-step, environmentally benign and reproducible biomineralization method. The Gd@Tf NPs Filter Unit with Ultracel-30 membrane (30 KDa), Millipore) at 5,000 rpm for 45 min to remove excess Gd$^{3+}$ in the supernatant. These purification procedures were repeated 3 times. The Gd content in the purified solution was determined by an X Series quadrupole inductively coupled plasma mass spectrometry instrument (ICP-MS, Thermo Elemental, Cheshire, U.K.). The stock solution was diluted to give the various concentrations required for the following experiments.

Characterization of Gd@Tf NPs

A drop of Gd@Tf solution was carefully applied to the carbon-coated copper grids and dried under vacuum at room temperature. High-resolution TEM measurements, for the determinations of morphology, microstructure, and energy spectra of Gd@Tf NPs, were performed with an FEI Tecnai G2 F20 microscope at an acceleration voltage of 200 kV. The mean hydrodynamic size and zeta potentials were monitored at 25° C. by DLS (Brookhaven Instruments Ltd., U.S.). A UV-3600 UV-Vis-NIR spectrophotometer (Shimadzu, Japan) was used to record absorption spectra with a slit width of 2.0 nm and a time constant of 2.0 s.

Relaxometry and MRI of a Gd@Tf Solution

The longitudinal relaxation times were measured with a 1.2 T MRI system (HT/MRSI60-60KY, Huantong Corporation, Shanghai, China) at room temperature. Gd@Tf NPs were dispersed in PBS to obtain different $Gd^{3+}$ concentrations (7.63-381.5 µM). The longitudinal relativity (r1) was defined as the slope of the linear fit for T1 relaxation rates (1/T1) versus Gd concentration. In vitro T1 weighted images were acquired with a 3.0 T MRI Scanner System (Discovery 750, GE Healthcare, USA) with a 32-channel phased array head coil. A standard spin echo imaging sequence was performed under the following parameters: TR/TE=400/16 ms, field of view=22×16.5 cm, slice thickness=1 mm; spacing=0.3 mm; matrix 512×256; NEX 2 and bandwidth 25 kHz.

Cytotoxicity Assay

Standard MTT assays were carried out to visualize the cytotoxicity of Gd@Tf NPs. PC-3 cells (TfR positive) were pre-seeded into 96-well cell culture plates and were incubated in RPMI-1640 cell medium supplemented with 10% fetal bovine serum (Thermo Fisher Scientific Inc., USA) at 37° C. in 5% $CO_2$. When the cells entered log phase growth, the medium was replaced with 200 µl of medium containing different concentrations of the prepared probe (0.00, 6.13, 12.25, 24.50, 49.00, or 98.00 µM). After 24 h incubation, the cells were washed three times with PBS; and MTT stock solution (5 mg/mL) was added to each well and left to react for 4 h. The medium was then discarded; and dimethyl sulfoxide (150 µL/well, Sigma-Aldrich, St. Louis, Mo., USA) was added to each well. The assay plate was placed on a shaker (QLBE, China) for 10 min, the optical density (OD) value for each well was recorded at 570 nm with a microplate reader (Thermo, Varioskan Flash). Cell viability was calculated by using the following formula: cell viability (%)=(mean OD of selected treatment group/mean OD of the control group)×100. Data is presented as the mean value with standard deviation from three independent experiments.

In Vitro MRI

Prostate tumor cells (PC-3) that were in log phase growth were seeded into a 6-well culture plate at a density of $3\times10^5$ cells per well until 80% of the cells had adhered to the well. The medium was replaced with RPMI-1640 cell medium (2 mL) containing Gd@Tf NPs at a concentration of 6 µM. After incubation for 4 h, the cells were washed three times with PBS (10 mM, pH 7.4) to remove any non-specifically bound Gd@Tf NPs. RPMI-1640 cell medium was added, and the cells were incubated for 24 h before they were collected again for counting. Under the same setup, a control was also performed in PBS only. Equal numbers of cells ($1.5\times10^6$) from the treated and the control groups were dispersed in water. Images were then obtained with a 3.0 T MRI Scanner System with the same parameters as described previously.

To study the exocytosis process of NPs, another 6-well plate of PC-3 cells were treated with Gd@Tf NPs or PBS. Equal numbers of cells were harvested, rinsed in PBS, resuspended, and analyzed by T1 MR scanning every 12 hours.

Competition Experiment

The targeting ability of Gd@Tf NPs toward TfR overexpressed by PC-3 was determined by a competition experiment with unconjugated Tf. PC-3 cells, incubated as described previously, were seeded into a 24-well culture plate. However, before replacing the medium with RPMI-1640 cell medium that contained Tf-labeled (6 µM of Gd) $Gd_2O_3$ NPs, an excess of unconjugated Tf (500 mg/mL) was first added to the medium and left to react for 2 h. The remaining procedures were performed as described above, and T1 MRI was performed.

Animal Model

Male 8-week-old BALB/c nude mice (25.0±1.0 g of body weight) were used in accordance with protocols approved by the Second Hospital of Tianjin Medical University on the ethical use of animals. To establish xenograft models of prostate cancer, single cell suspensions of PC-3 cells (about 1×106) in Matrigel (BD Biosciences; 1/1) were injected subcutaneously into the left shoulder of BALB/c nude mice. After ~2 weeks post-inoculation, tumors grew to ~0.8-1.0 cm in diameter, at which point further experiments were performed.

In Vivo MRI

Prior to imaging, tumor-bearing mice were anesthetized with an intraperitoneal injection of 5% chloral hydrate (7 mL/kg). Then, Gd@Tf NPs at a total dose of 60 µg Gd per mouse (0.015 mmol Gd/kg in 200 µL PBS) were administrated into the tail vein. Dynamic MRI was carried out before, and at sequential time points after injection with a 3.0 T MRI Scanner System equipped with a special coil for small animal imaging. The imaging parameters were as follows: TR/TE=400/15 ms, field of view=16×12 cm, slice thickness=1.5 mm; spacing=0.5 mm; matrix 512×256; NEX 2 and bandwidth 25 kHz. All images were processed with an Advantage Workstation 4.9 (AW4.9, GE Healthcare). To monitor the enhanced effect of the NPs, the signal intensity of a manually drawn region of interest (ROIs) at each imaging time point was measured 3 times. To further observe the metabolic pathway of Gd@Tf NPs, the faeces of mice with intravenous injection of Gd@Tf NPs or PBS were collected and their longitudinal relaxation times (or T1 values) were measured using inversion-recovery sequences of MR imaging.

In Vivo Toxicity Evaluation

To evaluate the biological effects of Gd@Tf NPs on the mice, their survival and body weight were closely monitored every other day after treatment of the prepared nanoprobes. Animals were euthanized after two weeks to monitor the histomorphological changes of major organs after the intravenous injection of Gd@Tf NPs. The brain, spleen, kidney, and liver were dissected from the mice and fixed in 4% formalin for 48 h, washed in PBS (3 times), embedded in paraffin, and sectioned (4-micron thick). Tissue sections were mounted onto glass slides, stained with hematoxylin/eosin for 5 min and examined under an optical microscope. Meanwhile, another group of mice treated with Gd@Tf NPs were chosen for blood routine examinations. Their blood samples were collected at 0 h, 1 h, 6 h, 12 h, 24 h, 48 h, 96 h, 7 days, and 14 days post-injection. A series of hematologic indexes, such as WBC, RBC, HGB, PLT, HCT, MCV, MCH, and MCHC, were analyzed using the Hemavet 950 FS (Drew Scientific, Inc., CT, USA). BALB/c nude mice that were intravenously treated with the same amount of PBS acted as the control group.

In Vivo Biodistribution Studies

To evaluate the biodistribution of Gd@Tf NPs in several related organs, tumor-bearing mice were sacrificed by cervical dislocation 9 h and 14 days post-injection. Major organs, such as liver, spleen, kidneys, lung, heart, and brain, and the tumors were harvested, pulverized, and treated with nitric acid. The resulting solutions were heated to 90° C. for 2 h and filtered. The Gd content in each filtrate was determined by an An X Series quadruple ICP-MS instrument.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A nanoparticle consisting of a human transferrin (Tf) protein and a gadolinium mineral, wherein
the gadolinium mineral is deposited within the tertiary structural of the human transferrin (Tf) protein and wherein the gadolinium mineral is one or more selected from $Gd_2O_3$, GdOOH, GdN, $GdPO_4$, $Gd(C_2O_4)$, $GdF_3$ and $Gd_2(CO_3)_3$.

2. The nanoparticle of claim 1, wherein the human transferrin (Tf) protein is biocompatible.

3. The nanoparticle of claim 1, wherein the human transferrin (Tf) protein is tumor targeting.

4. The nanoparticle of claim 1, wherein the human transferrin (Tf) protein is body-clearable.

5. The nanoparticle of claim 1, wherein the gadolinium mineral is $Gd_2O_3$.

6. A composition comprising the nanoparticle of claim 1.

7. A method for magnetic resonance imaging (MRI), comprising administering to a subject in need thereof a composition comprising the nanoparticle of claim 1.

8. A method for magnetic resonance imaging (MRI) and concomitant delivery of a therapeutic agent, comprising administering to a subject in need thereof a composition comprising the nanoparticle of claim 1.

* * * * *